(12) United States Patent  (10) Patent No.: US 6,580,087 B1
Suzuki et al.  (45) Date of Patent: Jun. 17, 2003

(54) INSPECTION APPARATUS

(75) Inventors: Yasuyuki Suzuki, Kanagawa (JP); Taketo Miyashita, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 09/688,532

(22) Filed: Oct. 16, 2000

(30) Foreign Application Priority Data

Oct. 15, 1999 (JP) .......................................... 11-294515

(51) Int. Cl.[7] .............................................. G01N 21/86
(52) U.S. Cl. .............................. 250/559.4; 250/559.45; 414/935
(58) Field of Search .............................. 250/221, 223 R, 250/559.4, 559.45, 559.29; 414/935, 936, 937, 938, 939, 940, 941

(56) References Cited

U.S. PATENT DOCUMENTS 5,674,039 A * 10/1997 Walker et al. ......... 414/222.05
6,133,576 A * 10/2000 Shafer et al. ............ 250/461.1
6,271,916 B1 * 8/2001 Marxer et al. ........... 356/237.3

* cited by examiner

Primary Examiner—Robert H. Kim
Assistant Examiner—Courtney Thomas
(74) Attorney, Agent, or Firm—Sonnenschein, Nath & Rosenthal

(57) ABSTRACT

An inspection apparatus in which the environment for inspecting a semiconductor wafer or the like at a high degree of cleanness to enable a fine pattern to be inspected properly. A main body portion 10 for inspecting the semiconductor wafer or the like is housed in the inside of a clean box 3 and clean air is supplied from the clean air unit 4 into the inside of the clean box 3 in which the main body portion 10 is accommodated. There are provided opening areas 80 in lateral sides of the clean box 3 lying laterally of the inspection stage 14 for the main body portion 10 and the vessel mounting space 8. The clean air supplied from the clean air unit 4 into the inside of the clean box is passed over the inspection stage carrying the semiconductor wafer and through the cassette 7b mounted in the vessel mounting space 8 so as to be discharged from the opening areas 80 to outside of the clean box 3. This effectively prohibits contaminants produced in the clean box 3 from being affixed to the semiconductor wafer mounted on the inspection stage 14 or to the semiconductor wafer loaded in the cassette 7b.

1 Claim, 10 Drawing Sheets

INSPECTION APPARATUS

RELATED APPLICATION DATA

The present application claims priority to Japanese Applications No. P11-294515 filed Oct. 15, 1999, which application is incorporated herein by reference to the extent permitted by law.

BACKGROUND OF THE INVENTION

1. Field of the Invention

This invention relates to an inspection apparatus used in inspecting a semiconductor wafer carrying a pre-set device pattern thereon.

2. Description of Related Art

A semiconductor device is fabricated by forming a fine device pattern on a semiconductor wafer. When forming such device pattern, it is a frequent occurrence that contaminants be affixed to the semiconductor wafer to produce grazing and resultant defects. The semiconductor wafer, suffering these flaws, prove a reject to lower the production yield.

That is, in order to stabilize the yield of a production line at a high level, it is desirable to locate the defects produced by contaminants or scratches to locate the cause to take effective measures on a production equipment or on a production process.

So, if a defect is located, an inspection apparatus is used to check the type of the defect for classification to identify the equipment or process responsible for the defect. The inspection apparatus for checking into the defect type is like an optical microscope and views the defect to an enlarged scale to identify the defect.

Meanwhile, if contaminants are affixed to the semiconductor wafer being inspected, proper inspection cannot be executed. So, the inspection of a semiconductor wafer needs to be executed in a clean environment.

For maintaining a clean environment in which to carry out semiconductor wafer inspection, such a method is effective in which a main body portion of the inspection apparatus be covered by a clean box and in which the interior of the clean box be kept to a high degree of cleanliness. If, in such case, the semiconductor wafer to be inspected is transported in a hermetically sealed vessel and the semiconductor wafer is moved by this vessel into the clean box, it is possible to prevent the contaminants effectively from being affixed to the semiconductor wafer to carry out the inspection of the semiconductor wafer properly without the necessity of maintaining the entire environment for the inspection apparatus at a high degree of cleanliness.

Meanwhile, the device pattern of a semiconductor wafer to be inspected is becoming finer with progress in improving the integration degree of the semiconductor device, such that recently the design rule is as fine is 0.18 $\mu$m or less. In inspecting this fine pattern, contaminants of extremely small size, which raised no serious problems in the past, now may be a factor obstructing proper inspection. It is therefore necessary to maintain the environment of inspection at a higher degree of cleanliness, in order to carry out proper inspection of the fine device pattern, such that, if extremely small contaminants are produced in the course of the inspection, these may be effectively prevented from being affixed to the semiconductor wafer.

SUMMARY OF THE INVENTION

It is therefore an object of the present invention to provide an inspection apparatus whereby a highly clean environment is realized to enable proper inspection of a fine device pattern.

The present inventors have conducted eager searches for accomplishing the above object, and have found that, by supplying clean air into the clean box and by properly controlling the stream of the clean air supplied into this clean box, it is possible to prevent contaminants such as fine dust effectively from becoming affixed to the article being inspected to achieve the inspection of fine patterns satisfactorily.

According to the present invention, there is provided an inspection apparatus including a main body portion for inspecting an article for inspection, a clean box for accommodating the main body portion therein and an air supplying unit for furnishing clean air into the inside of the clean box, in which the main body portion is provided with an inspection stage for setting the article for inspection thereon and a cassette accommodation portion for carrying therein a cassette in which the article for inspection is loaded, and in which there are provided opening areas in at least portions of a lateral surface of the clean box located laterally of the inspection stage and the cassette accommodation portion for allowing clean air supplied from the air supplying unit into the inside of the clean box to be passed over the inspection stage 14 and through the cassette loaded in the cassette accommodation portion so as to be discharged to outside the clean box.

In the inspection apparatus according to the present invention, the interior of the clean box in which to hold the main body portion of the apparatus is kept in a clean environment by clean air supplied thereto from the air supply unit. In this inspection apparatus, there are provided opening areas in at least portions of the lateral sides of the clean box lying laterally of the inspection stage and the cassette accommodating portion provided in the main body portion, so that the clean air supplied from the air supply unit to the inside of the clean box is passed through the inspection stage carrying the article to be inspected and through the cassette housed in the cassette accommodating portion so as to be discharged to outside the clean box. This effectively prevents contaminants produced in the clean box from becoming attached to the article for inspection mounted on the inspection stage or to the article for inspection loaded in the cassette accommodation portion to enable the article to be inspected properly by the main body portion.

Preferably, the clean box is provided with a jutting portion at approximately the same height level as the lower, end of the inspection stage. The jutting portion is protruded towards the main body portion. By providing the jutting portion at approximately the same height level as the lower end of the inspection stage, the clean air supplied from the air supplying unit into the clean box can be routed properly over the inspection stage.

Preferably, an inclined guide portion for routing clean air supplied from the air supplying portion into the clean box into the cassette loaded in the cassette accommodating portion is provided in the vicinity of the cassette accommodating portion in the main body portion. By providing the inclined guide portion in the vicinity of the cassette accommodating portion in the clean box, the clean air supplied from the air supplying unit into the clean box can be routed properly into the cassette.

Also preferably, an inspection stage on which the article for inspection is set is provided in the main body portion, whilst there is provided a partitioning wall section between the inspection stage and the cassette accommodating portion for partitioning the inspection stage and the area of the cassette accommodating portion from each other. By providing the partitioning wall section between the inspection stage and the cassette accommodating portion, it is possible to prevent contaminants such as dust produced in the area of the inspection stage from intruding into the area of the cassette accommodating portion to prevent the contaminants from becoming attached to the article loaded in the cassette.

In the inspection apparatus according to the present invention, there are provided opening areas in at least portions of the lateral sides of the clean box lying laterally of the inspection stag and the cassette accommodating portion provided in the main body portion, so that the clean air supplied from the air supply unit to the inside of the clean box is passed through the inspection stage carrying the article to be inspected and through the cassette housed in the cassette accommodating portion so as to be discharged to outside the clean box. This effectively prevents contaminants produced in the clean box from becoming attached to the article for inspection mounted on the inspection stage or to the article for inspection loaded in the cassette accommodating portion to enable the article to be inspected properly by the main body portion.

DESCRIPTION OF THE PREFERRED EMBODIMENTS

Figure 1:
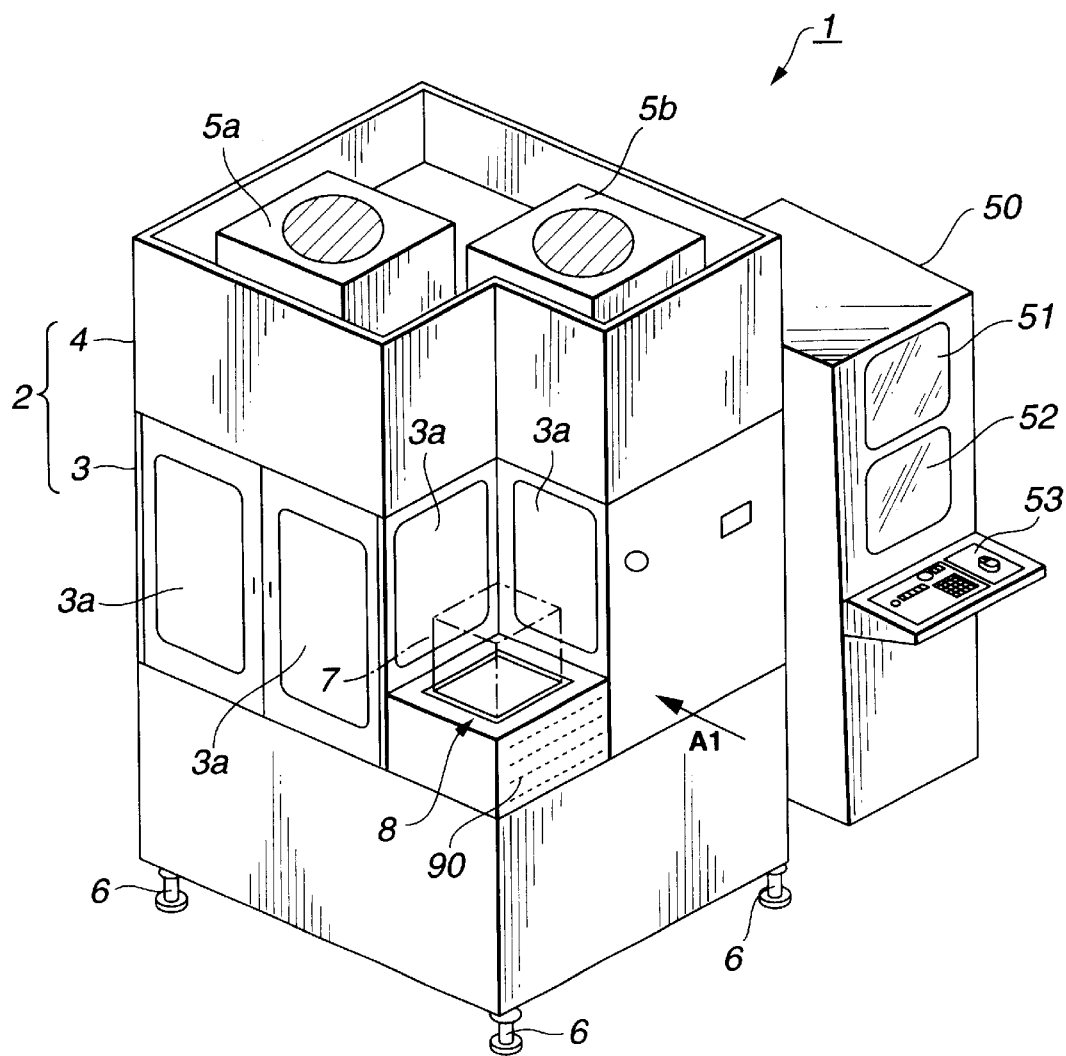
FIG. 1 is an overall perspective view showing an inspection apparatus according to the present invention.

Referring to the drawings referred embodiments of according to the present invention will be explained in detail.

The overall appearance of an inspection apparatus 1 embodying the present invention is shown in FIG. 1. This inspection apparatus 1 is used for inspecting a semiconductor wafer having a pre-set device pattern formed thereon. Specifically, when a defect is found in a device pattern formed on a semiconductor wafer, this inspection apparatus 1 checks the type of the defect by way of classification.

Referring to FIG. 1, the inspection apparatus 1 has a clean unit 2 used for maintaining a clean environment in which to conduct semiconductor wafer inspection. This clean unit 2 includes a clean box 3 in the form of a hollow box obtained on bending a stainless steel plate and a clean air unit 4 formed integrally with the upper part of the clean box 3.

The clean box 3 has a window 3a at a pre-set portion whereby an inspector is able to view and inspect the interior of the clean box 3.

The clean air unit 4 is used for supplying clean air into the inside of the clean box 3 and includes two blowers 5a, 5b arranged at two different upper positions of the clean box 3, and an air filter, not shown, arranged between the blowers 5a, 5b and the clean box 3. The air filter is a high performance air filter, such as a HEPA filter (high efficiency particulate air filter) or an ULPA filter (ultra low penetration air filter). This clean air unit 4 removes contaminants in air supplied by the blowers 5a, 5b by the high performance air filter to produce clean air which is supplied into the clean box 3.

In the inspection apparatus 1 of the present invention, the volume of clean air supplied from the clean air unit 4 into the clean box 3 is separately controlled for each of the blowers 5a, 5b to optimally control the air stream in the clean box 3, as will be explained subsequently in detail. Although an embodiment is explained here in which the clean air unit 4 has the two blowers 5a, 5b, the number of the blowers may be determined depending on the size or the shape of the clean box 3. For example, three or more blowers may be used, if so desired. In the latter case, the volume of clean air supplied into the clean box 3 from the clean air unit 4 is controlled independently from blower to blower before the clean air is discharged from the lower end of the clean box 3 to outside the clean box 3.

The clean box 3 is carried by support legs 6 on a floor plate and has its lower end opened so that air supplied from the clean air unit 4 into the inside of the clean box 3 is discharged via this lower end of the clean box 3 to outside the clean box 3. In the lateral surface of the clean box 3 are formed opening areas at pre-set areas thereof, as will be explained subsequently in detail, so that air supplied from the clean air unit 4 into the inside of the clean box 3 is discharged to outside via these opening areas in the lateral surface of the clean box 3 as well.

The clean unit 2 perpetually furnishes clean air from the clean air unit 4 into the clean box 3 to discharge air circulated through the inside of the clean box 3 as an air stream to outside the clean box 3. This discharges contaminants generated in the clean box 3 to outside the clean box 3 along with air to maintain the inner environment in the clean box 3 to an extremely high degree of cleanness of the order of class 1.

The air pressure in the clean box 3 is perpetually maintained at a positive pressure in order to prevent air containing contaminants from outside into its inside.

Figure 2:
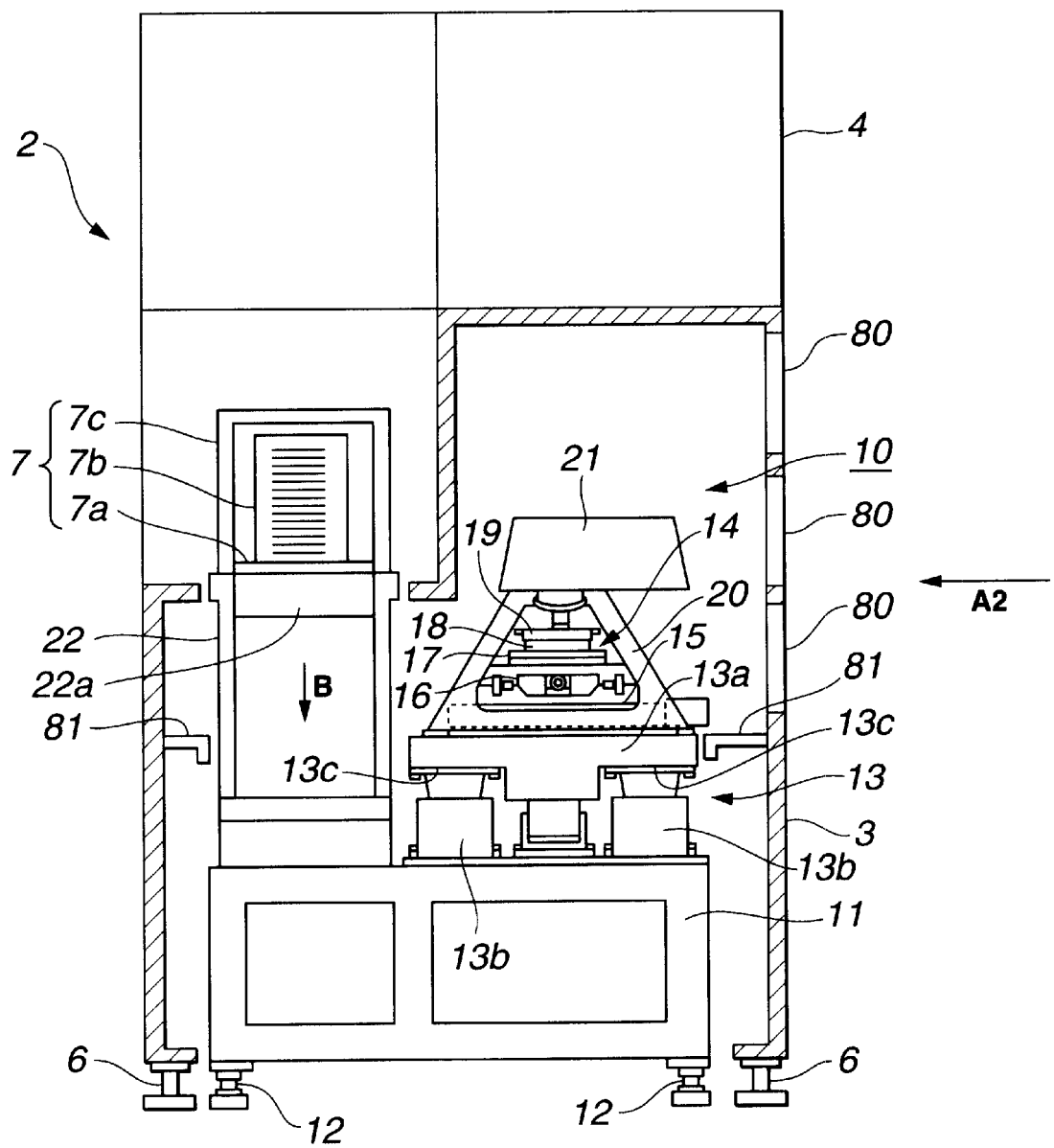
FIG. 2 shows the inside of a main body portion of the apparatus, arranged in the interior of a clean box of the inspection apparatus, looking from the direction of an arrow A1 in FIG. 1.

In this inspection apparatus 1, the main body portion 10 is accommodated in the clean box 3 within which a semiconductor wafer carrying a pre-set device pattern is to be inspected by the main body portion 10, as shown in FIG. 2. The semiconductor wafer to be inspected is transported in the pre-set hermetically sealed vessel 7 through which the semiconductor wafer is transferred into the inside of the clean box 3. Meanwhile, FIG. 2 shows the inside of the clean box 3 as seen from the direction of arrow A1 in FIG. 1.

The vessel 7 includes a bottom 7a, a cassette 7b secured to the bottom 7a and a cover 7c detachably engaged with the bottom 7a to overlie the cassette 7b. A plurality of semiconductor wafers being inspected are loaded on the cassette 7b in a stacked state at a pre-set distance from each other and are hermetically sealed by the bottom 7a and the cover 7c.

In inspecting semiconductor wafers, the vessel 7, in which the semiconductor wafers are accommodated, is installed in a vessel mounting space 8 provided at a pre-set position of the clean box 3.

In the vessel mounting spate 8, a lift base 22a of an elevator 22, which will be explained subsequently, is mounted so that the upper surface of the floor 22a faces outside of the clean box 3, whilst the vessel 7 is mounted in the vessel mounting space. 8 so that its bottom 7a is positioned on the lift base 22a of the elevator 22.

When the vessel 7 is mounted in the vessel mounting space 8, the bottom 7a of the vessel 7 is disengaged from the cover 7c. By the base 20a of the elevator 20 being lowered in the direction indicated by arrow B in FIG. 2, the bottom 7a of the vessel 7 and the cassette 7b are separated from the cover 7c and moved into the inside of the clean box 3. This transports the semiconductor wafer to be inspected into the inside of the clean box 3 without being exposed to atmosphere.

That is, the bottom 7a of the vessel 7, thus moved into the inside of the clean box 3, serves as a cassette mounting portion in the clean box 3.

When the semiconductor wafer is transferred into the inside of the clean box 3, the semiconductor wafer to be inspected is taken out from the cassette 7b by a transporting robot 23, as later explained, for inspection.

In the inspection apparatus 1, in which semiconductor wafers are inspected in the interior of the clean box 3 maintained at a high degree of cleanness, it is possible to evade the inconvenience that contaminants become attached to the semiconductor wafer at the time of inspection to obstruct proper inspection. Moreover, since the semiconductor wafer to be inspected is transported as it is charged into the hermetically sealed vessel 7, and the semiconductor wafer is transported into the inside of the clean box 3 through this vessel 7, it is possible to prevent contaminants effectively from becoming deposited on the semiconductor wafer, if only the inside of the clean box 3 and the inside of the vessel 7 are maintained at a sufficient degree of cleanliness, without it being necessary to elevate the degree of cleanness of the entire environment in which the inspection apparatus 1 is mounted.

By locally elevating only the degree of cleanliness of the necessary location, the high degree of cleanness can be realized at the same time as the cost for realizing the clean environment can be lowered appreciably. Meanwhile, as the mechanical interface between the hermetically sealed vessel 7 and the clean box 3, a so-called SMIF (standard mechanical interface) may be used with advantage. In this case, a so-called SMIF-POD is used as the hermetically sealed vessel 7.

This inspection apparatus 1 is provided with an external unit 50, in which a mounted e.g., a computer for actuating the main body portion 10, as shown in FIG. 1. This external unit 50 is mounted outside the clean box 3. This external unit 50, is provided with a display unit 51 for demonstrating an image which has photographed the semiconductor wafer, a display unit 52 for demonstrating the various conditions at the time of inspection and an inputting device 53 for inputting commands to the main body portion 10. An inspector of a semiconductor wafer inputs necessary commands from the inputting device 53 provided on the external unit 50 to inspect the semiconductor wafer as he views the display units 51, 52 mounted on the external unit 50.

The main body portion 10, provided in the clean box 3, is now explained in detail.

The main body portion 10 includes a support base 11, as shown in FIG. 2. This support base 11 is a base used for supporting various units of the main body portion 10. The bottom of the support base 11 includes support legs 12. The support base 11 and various units carried thereby are adapted for being supported on a floor plate by these support legs 12 independently of the clean box 3.

On the support base 11, an inspection stage 14, on which to set a semiconductor wafer to be inspected, is provided through a vibration removing table 13.

The vibration removing table 13 is designed to suppress vibrations from the floor or those produced on movement of the inspection stage 14, and includes a stone block 13a on which the inspection stage 14 is mounted and plural movable legs 13b carrying the stone block 13a. On generation of vibrations, the vibration removing table 13 senses these vibrations to actuate the movable legs 13b to cancel the vibrations of the stone block 13a and the inspection stage 14 mounted thereon promptly.

In the present inspection apparatus 1, even the slightest vibrations sometimes obstruct the inspection, because it is the semiconductor wafer carrying fine device patterns that is to be inspected. In particular, since the present inspection apparatus 1 performs the inspection at a high resolution, using the UV light, the effect of the vibrations tends to present itself significantly. Therefore, in the present inspection apparatus 1, the inspection stage 14 is mounted on the vibration removing table 13, so that, even if the slightest vibrations are produced on the inspection stage 14, these vibrations are cancelled quickly to suppress the effect of vibrations to improve the inspection performance at a high resolution with the use of the UV light.

For mounting the inspection stage 14 in stability on the vibration removing table 13, it is desirable that the center of gravity of the vibration removing table 13 be at a more or less lower position. So, in the present inspection apparatus 1, a cut-out 13c is provided at a lower end of the stone block 13a and the movable legs 13b are adapted for supporting the stone block 13a at these cut-outs 13c to lower the center of gravity of the vibration removing table 13.

The vibrations etc produced on movement of the inspection stage 14 can be predicted to a certain extent at the outset. If these vibrations are predicted at the outset to actuate the vibration removing table 13, it is possible to prevent the vibrations otherwise produced in the inspection stage 14. It is therefore desirable to predict the vibrations etc produced in moving the inspection stage 14 at the outset to actuate the vibration removing table 13.

The inspection stage 14 is a stage used for supporting the semiconductor wafer being inspected. This inspection stage 14 has the function of both supporting the semiconductor wafer to be inspected and moving the semiconductor wafer to a pre-set inspection position.

Specifically, the inspection stage 14 includes an X-stage 15, mounted on the vibration removing table 13, a Y-stage 16, mounted on the X-stage 15, a θ-stage 17, mounted on the Y-stage 16, a Z-stage 18, mounted on the θ-stage 17, and a suction plate 19 mounted on the Z-stage 18.

The X-stage 15 and the Y-stage 16 are stages moved in the horizontal direction and cause the semiconductor wafer being inspected to be moved in a direction perpendicular to each other to guide the device pattern being inspected to a pre-set inspection position.

The θ-stage 17 is a so-called rotary stage and is adapted for rotating the semiconductor wafer. In inspecting the semiconductor wafer, the wafer is rotated by the θ-stage 17 so that the device pattern on the semiconductor wafer will be horizontal or vertical relative to the screen.

The Z-stage 18 is a stage moved in the perpendicular direction for adjusting the stage height. In inspecting the semiconductor wafer, the stage height is adjusted by the Z-stage 18 to give a proper height of the inspection surface of the semiconductor wafer.

The suction plate 19 is used to suck and secure the semiconductor wafer being inspected. In inspecting the semiconductor wafer, the wafer being inspected is placed on and sucked by this suction plate 19 to suppress its unneeded movements.

On the vibration removing table 13 is mounted an optical unit 21 supported by the support member 20 so that the optical unit 21 will overlie the inspection stage 114. The optical unit 21 is used for photographing an image of the semiconductor wafer at the time of inspection of the semiconductor wafer. The optical unit 21 has the function of photographing an image of the semiconductor wafer being inspected at a low resolution using visible light and the function of photographing an image of the semiconductor wafer being inspected at a high resolution using the UV light.

Figure 3:
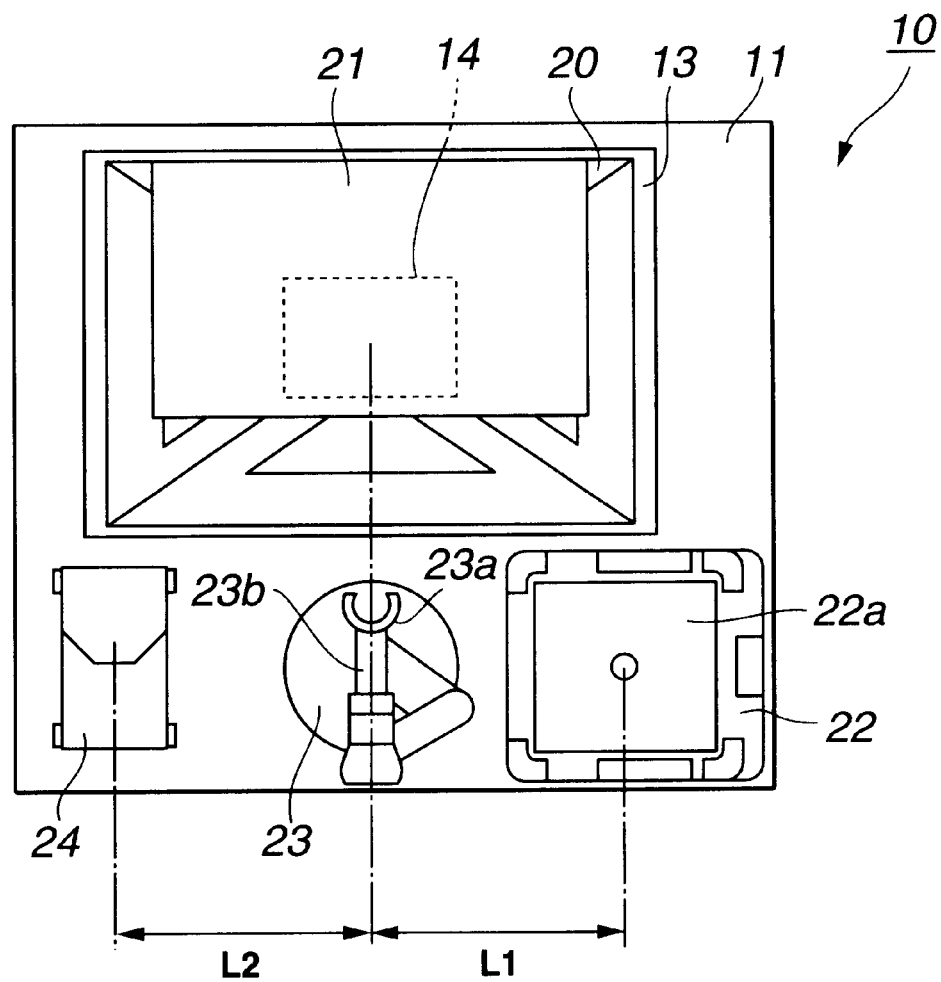
FIG. 3 is a schematically plan view of the main body portion of the inspection apparatus, looking from above the apparatus.

On the support base 11 is mounted an elevator 22 for taking out the cassette 7b having loaded therein the semiconductor wafer being inspected from the vessel 7 to move it into the clean box 3, as shown in FIGS. 2 and 3. On the support base 11, there are mounted the transporting robot 23 for transporting the semiconductor wafer and a pre-aligner 24 for centering and phasing the semiconductor wafer before setting the semiconductor wafer on the inspection stage 14, as shown in FIG. 3. Meanwhile, FIG. 3 is a plan view showing the main body portion 10 from above.

The elevator 22 has a lift base 22a for performing uplifting and lowering movements. When the vessel 7 is set in the vessel mounting space 8 of the clean box 3 to disengage the bottom 7a of the vessel 7 from the cover 7c, and the lift base 22a is lowered, the bottom 7a of the vessel 7 and the cassette 7b secured thereto are moved into the inside of the clean box 3.

The transporting robot 23 includes an actuating arm 23b having an end suction unit 23a. This actuating arm 23b is moved to suck the semiconductor wafer by the end suction unit 23a to transport the semiconductor wafer in the clean box 3.

The pre-aligner 24 phases and centers the semiconductor wafer with an orientation flat and a notch previously provided to the semiconductor wafer. In the inspection apparatus 1, the semiconductor wafer is phased by the pre-aligner 24, before the semiconductor wafer is set on the inspection stage 14, in order to improve the inspection efficiency.

In placing the semiconductor wafer on the inspection stage 14, the bottom 7a of the vessel 7 and the cassette 7b are moved into the inside of the clean box 3 by the elevator 22. From among the plural semiconductor wafers, loaded in the cassette 7b, the semiconductor wafer to be inspected is selected and taken out by the transporting robot 23 from the cassette 7b.

The semiconductor wafer, taken out from the cassette 7b, is transported by the transporting robot 23 to the pre-aligner 24. The semiconductor wafer transported to the pre-aligner 24 is thereby phased or centered and transported by the transporting robot 23 to the inspection stage 14 where it is set on the suction plate 19 for inspection.

When the semiconductor wafer to be inspected is transferred to the inspection stage 14, the semiconductor wafer to be inspected next is taken out by the transporting robot 23 from the cassette 7b and transported to the pre-aligner 24. During the time the semiconductor wafer previously transported to the inspection stage 14 is inspected, the semiconductor wafer to be inspected next is phased and centered. When the inspection of the semiconductor wafer previously transported to the inspection stage 14 comes to a close, the semiconductor wafer to be inspected next is quickly transported to the inspection stage 14.

In the inspection apparatus 1 in which, before transporting the semiconductor wafer being inspected to the inspection stage 14, the pre-aligner 24 performs phasing and centering, it is possible to shorten the time needed in positioning the semiconductor wafer by the inspection stage 14. Moreover, in the inspection apparatus 1, in which the semiconductor wafer to be inspected next is taken out from the cassette 7b for phasing and centering by the pre-aligner 24, during the time of inspection of the inspection of the semiconductor previously transported to the inspection stage 14, it is possible to shorten the processing time as a whole to realize efficient inspection.

Meanwhile, in the present inspection apparatus 1, the elevator 22, transporting robot 23 and the pre-aligner 23 are arranged on the support base 11 on a bee line, as shown in FIG. 3. The setting positions of the elevator 22, transporting robot 23 and the pre-aligner 23 are determined so that the distance L1 between the elevator 22 and the transporting robot 23 will be approximately equal to the distance L2 between the transporting robot 23 and the pre-aligner 24. Moreover, the inspection stage 14 is positioned substantially at right angles to the arraying direction of the elevator 22 and the pre-aligner 24 looking from the transporting robot 23.

In the inspection apparatus 1, in which the respective components are arranged as described above, the semiconductor wafer to be inspected can be transported promptly and accurately.

That is, in the present inspection apparatus 1, the distance L1 between the elevator 22 and the transporting robot 23 is approximately equal to the distance L2 between the transporting robot 23 and the pre-aligner 24, the semiconductor wafer taken out from the cassette 7b can be transported to the pre-aligner 24 without changing the length of the arm 23b and the transporting robot 23. Thus, in the present inspection apparatus 1, since an error etc produced on changing the length of the arm 23b of the transporting robot 23 is not problematical, the operation of transporting the semiconductor wafer to the pre-aligner 24 can be performed correctly. Moreover, since the elevator 22, transporting robot 23 and the pre-aligner 24 are arrayed linearly, the transporting robot 23 is able to transport the semiconductor wafer taken out from the cassette 7b to the pre-aligner 24 solely by the linear movement of the transporting robot 23. So, with the present inspection apparatus 1, the operation of transporting the semiconductor wafer to the pre-aligner 24 can be performed extremely correctly and promptly.

Moreover, in the present inspection apparatus 1, since the inspection stage 14 is arranged in a direction substantially at right angles to the arraying direction of the elevator 22 and the pre-aligner 24, when looking from the transporting robot 23, the semiconductor wafer can be transported to the inspection stage 14 by the transporting robot 23 performing a linear movement. So, in the present inspection apparatus 1, the operation of transporting the semiconductor wafer to the inspection stage 14 can be performed extremely correctly and promptly. In particular, in the present inspection apparatus 1, in which the semiconductor wafer carrying a fine device pattern is to be inspected, the semiconductor wafer to be inspected needs to be transported and positioned extremely correctly, the above-described arrangement is extremely effective.

Figure 4:
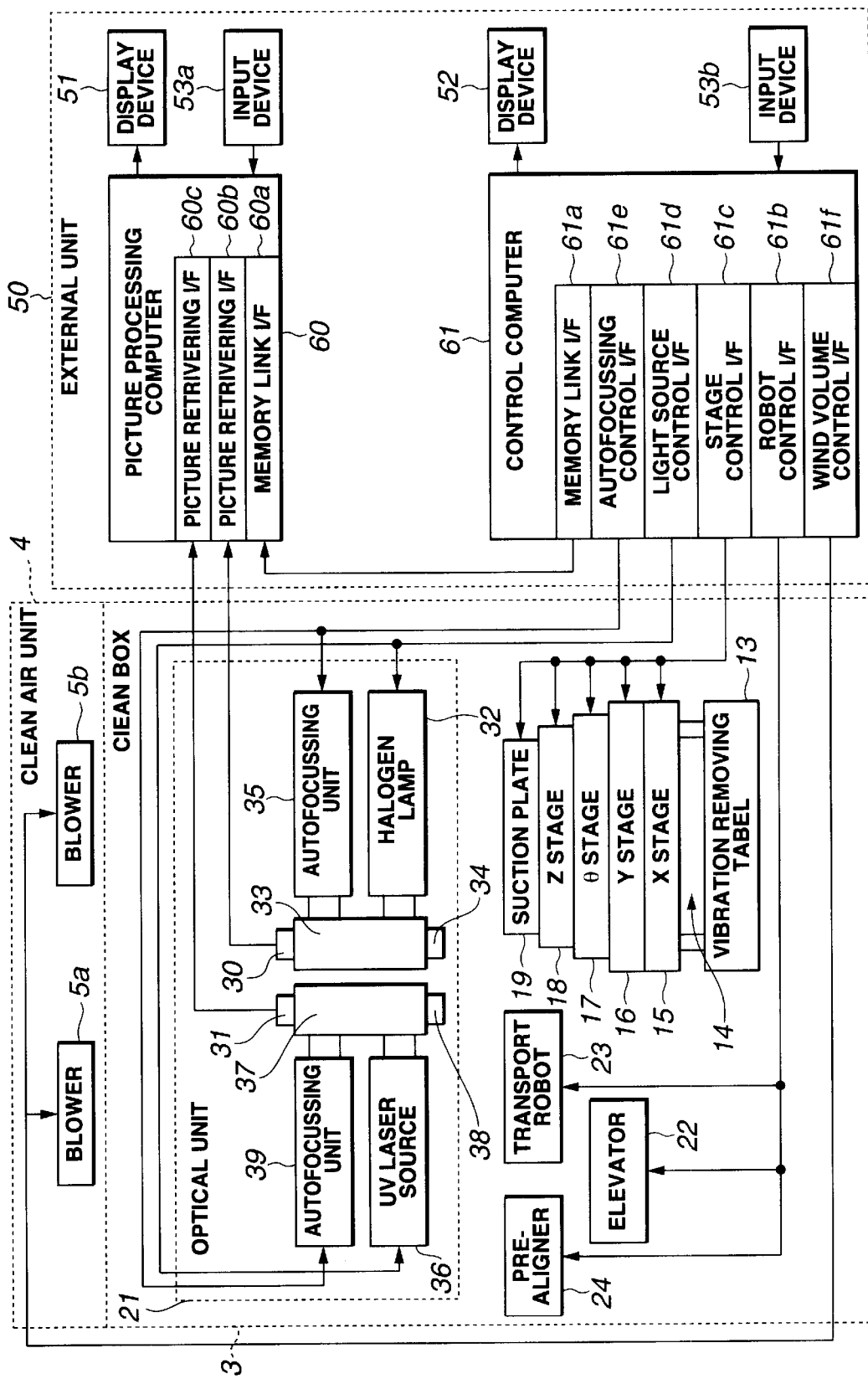
FIG. 4 is a block diagram showing an illustrative structure of the inspection apparatus.

Referring to the block diagram of FIG. 4, the inspection apparatus 1 is explained more specifically.

Referring to FIG. 4, the external unit 50 of the inspection apparatus 1 includes a image processing computer 60, to which are connected the display unit 51 and an input device 53a, and a control computer 61, to which are connected the display unit 52 and an input device 53b. Meanwhile, in FIG. 1, the input device 53a, connected to the image processing computer 60, and the input device 53b, connected to the control computer 61, are collectively termed an inputting device 53.

The image processing computer 60 is a computer for retrieving and processing an image which has photographed a semiconductor wafer by CCD (charge-coupled device) cameras 30, 31 provided in the optical unit 21, in inspecting the semiconductor wafer. That is, in the present inspection apparatus 1, an image of the semiconductor wafer photographed by the CCD cameras 30, 31 installed in the optical unit 21 is processed and analyzed by the image processing computer 60 to inspect the semiconductor wafer.

Meanwhile, the inputting device 53a, connected to the image processing computer 60, is used to input commands necessary to analyze a image retrieved from the CCD cameras 30, 31 to the image processing computer 60, and may, for example, be a pointing device, such as a mouse, or a keyboard. The display unit 51, connected to the image processing computer 60, is used for demonstrating the results of analyses of the image retrieved from the CCD cameras 30, 31, and may, for example, be a CRT display or a liquid crystal display.

In inspecting a semiconductor wafer, the control computer 61 controls the inspection stage 14, elevator 22, transporting robot 23, pre-aligner 24 and inner components in the optical unit 21. That is, in the present inspection apparatus 1, the control computer 61 controls the inspection stage 14, elevator 22, transporting robot 23, pre-aligner 24 and inner equipment in the optical unit 21, so that an image of the semiconductor wafer being inspected will be photographed by the CCD cameras 30, 31 provided in the optical unit 21.

The control computer 6i has the function of controlling blowers 5a, 5b of the clean air unit 4. That is, in the present inspection apparatus 1, the control computer 61 controls the blowers 5a, 5b of the clean air unit 4 to furnish clean air into the clean box 3 at all times during inspection of the semiconductor wafer as well as to control an air stream in the clean box 3.

Meanwhile, the inputting device 53b, connected to the control computer 61, is used to input commands necessary to control the inspection stage 14, elevator 22, transporting robot 23, pre-aligner 24, respective components in the optical unit 21, and the blowers 5a, 5b of the clean air unit 4, to the control computer 61, and may, for example, be a pointing device, such as a mouse, or a keyboard. A display unit 52, connected to the control computer 61, is used for demonstrating various conditions at the time of inspecting semiconductor wafers, and may, for example, be a CRT display or a liquid crystal display.

The image processing computer 60 and the control computer 61 are able to exchange data with each other through a memory link mechanism. That is, image processing computer 60 and the control computer 61 are interconnected through respective memory link interfaces 60a, 61a, to enable data exchange between the image processing computer 60 and the control computer 61.

In the interior of the clean box 3 of the inspection apparatus 1, there are provided the elevator 22, transporting robot 23 and the pre-aligner 24, as mentioned above, as a mechanism for taking out a semiconductor wafer transported as it is charged in the hermetically sealed vessel 7 from the cassette 7b of the vessel 7 for setting the wafer so taken out on the inspection stage 14. These components are connected to the control computer 61 provided on the external unit 50 through a robot control interface 61b. The elevator 22, transporting robot 23 and the pre-aligner 24 are fed with control signals from the control computer 61 through the robot control interface 61b.

That is, when the semiconductor wafer, transported as it is charged in the hermetically sealed vessel 7, is to be taken out from the cassette 7b of the vessel 7 and set on the inspection stage 14, control signals are sent from the control computer 61 through the robot control interface 61b to the elevator 22, transporting robot 23 and the pre-aligner 24. The elevator 22, transporting robot 23 and the pre-aligner 24 are actuated based on these control signals to take out the semiconductor wafer, transported as it is charged in the hermetically sealed vessel 7, from the cassette 7b of the vessel 7, to phase and center the semiconductor wafer by the pre-aligner 25 and to set the wafer in the inspection stage 14.

In the clean box 3 of the inspection apparatus 1 is mounted a vibration removing table 13, on which is mounted the inspection stage 14 comprising the X-stage 15, Y-stage 16, θ-stage 17, Z-stage 18 and the suction plate 19.

The X-stage 15, Y-stage 16, θ-stage 17, Z-stage 18 and the suction plate 19 are connected through a stage control interface 61c to the control computer 61 mounted on the external unit 50. The X-stage 15, Y-stage 16, θ-stage 17, Z-stage 18 and the suction plate 19 are fed with control signals from the control computer 61 through the stage control interface 61c.

That is, in inspecting the semiconductor wafer, control signals are sent from the control computer 61 to the X-stage 15, Y-stage 16, θ-stage 17, Z-stage 18 and the suction plate 19 through the stage control interface 61c. The X-stage 15, Y-stage 16, θ-stage 17, Z-stage 18 and the suction plate 19 are actuated based on these control signals to suck and secure the semiconductor wafer being inspected by the suction plate 19 to move the semiconductor wafer to a pre-set position, angle and height by the X-stage 15, Y-stage 16, θ-stage 17 and the Z-stage 18.

On the vibration removing table 13 is also mounted the optical unit 21, as mentioned above. The optical unit 21, adapted for photographing an image of the semiconductor wafer in inspecting the semiconductor wafer, has the function of photographing an image of a semiconductor wafer at the time of inspection of a semiconductor wafer at a low resolution using the visible light, and the function of photographing an image of a semiconductor wafer at the time of inspection of the semiconductor wafer at a high resolution using the UV light.

Within the interior of the optical unit 21, there are arranged, as a mechanism for photographing an image of the semiconductor wafer by the visible light, a CCD camera for visible light 30, a halogen lamp 32, an optical system for visible light 33, an objective lens for visible light 34 and an autofocussing unit for visible light 35.

In photographing an image of the semiconductor wafer with visible light, the halogen lamp 32 is turned on. It is noted that a driving source for the halogen lamp 32 is connected through a light source control interface 61d arranged in the external unit 50. The driving source for the halogen lamp 32 is fed with control signals from the control computer 61 through the light source control interface 61d. The halogen lamp 32 is turned on or off based on these control signals.

In photographing an image of the semiconductor wafer using the visible light, the halogen lamp 32 is lit and the visible light from the halogen lamp 32 is illuminated on the semiconductor wafer through the optical system for visible light 33 and the objective lens for visible light 34 to illuminate the semiconductor wafer. An image of the semiconductor wafer lit by the visible light is enlarged by the objective lens for visible light 34, with the image thus enlarged being then photographed by the CCD camera for visible light 30.

The CCD camera for visible light 30 is connected through an image retrieving interface 60b to the image processing computer 60 mounted in the external unit 50. The image of the semiconductor wafer, photographed by the CCD camera for visible light 30, is retrieved through the image retrieving interface 60b into the image processing computer 60.

In photographing an image of a semiconductor wafer with the visible light as described above, autofocussing is executed by the autofocussing unit for visible light 35. That is, the autofocussing unit for visible light 35 is used to check whether or not the distance between the objective lens for visible light 34 and the semiconductor wafer coincides with the focal length of the objective lens for visible light 34 and, in case of non-coincidence, the objective lens for visible light 34 or the Z-stage 18 is moved until the surface of the semiconductor wafer to be inspected coincides with the focal plane of the objective lens for visible light 34.

The autofocussing unit for visible light 35 is connected through an autofocussing control interface 61e to the control computer 61 mounted on the external unit 50. The autofocussing unit for visible light 35 is fed with control signals from the control computer 61 through the autofocussing control interface 61e. The autofocussing of the objective lens for visible light 34 by the autofocussing unit for visible light 35 is performed on the basis of these control signals.

Within the interior of the optical unit 21, there are mounted, as a mechanism for photographing an image of the semiconductor wafer by the UV light, a CCD camera for UV light 31, a light source for UV laser light 36, an optical system for UV light 37, an objective lens for UV light 381 and an autofocussing controller for UV light 39.

When photographing an image of the semiconductor wafer with the UV light, the light source for UV laser light 36 is turned on. The driving source for the light source for UV laser light 36 is connected through the light source control interface 61d to the control computer 61 arranged in the external unit 50. The driving source for the light source for UV laser light 36 is fed with control signals from the control computer 61 through the light source control interface 61d.

As the light source for UV laser light 36, such a light source emitting the UV laser light with a wavelength of the order of 266 nm is preferably employed. The UV laser light, with the wavelength of the order of 266 nm, is obtained as fourth harmonics of the YAG laser. As the laser light source, such as laser light source emitting the laser light with the wavelength of the order of 166 nm, has been developed. This latter laser light source may also be used as the light source for UV laser light 36.

In photographing an image of the semiconductor wafer with the UV light, the light source for UV laser light 36 is lit, and the UV light from this light source for UV laser light 36 is illuminated on the semiconductor wafer through the optical system for UV light 37 and the objective lens for UV light 38 to illuminate the semiconductor wafer. An image of the semiconductor wafer, illuminated by the UV light, is enlarged by the objective lens for UV light 38 and the resulting image is photographed by the CCD camera for UV light 31.

It is noted that the CCD camera for UV light 31 is connected through an image retrieving interface 60c to the image processing computer 60. An image of the semiconductor wafer, photographed by the CCD camera for UV light 31, is retrieved through the image retrieving interface 60c by the image processing computer 60.

In photographing an image of the semiconductor wafer with the UV light as described above, the autofocussing is made using the autofocussing controller for UV light 39. That is, using the autofocussing controller for UV light 39, it is detected whether or not the separation between the objective lens for UV light 38 and the semiconductor wafer coincides with the focal length of the objective lens for UV light 38. In case of non-coincidence, the objective lens for UV light 38 or the Z-stage 18 is moved until the surface of the semiconductor wafer to be inspected coincides with the focal plane of the objective lens for UV light 38.

The autofocussing controller for UV light 39 is connected to the control computer 61 provided in the external unit 50 through the autofocussing control interface 61e. The autofocussing controller for UV light 39 is fed with control signals from the control computer 61 through the autofocussing control interface 61e. The autofocussing of the objective lens for UV light 38 by the autofocussing controller for UV light 39 is achieved on the basis of these control signals.

The clean air unit 4 is provided with the two blowers 5a, 5b, as described above. These blowers 5a, 5b are connected through a wind volume control interface 61 of the control computer 61 provided in the external unit 50. The blowers 5a, 5b of the clean air unit 4 are fed with control signals from the control computer 61 through the wind volume control interface 61f. The control of the number of revolutions or on/off switching of the blowers 5a, 5b is executed on the basis of these control signals.

Figure 5:
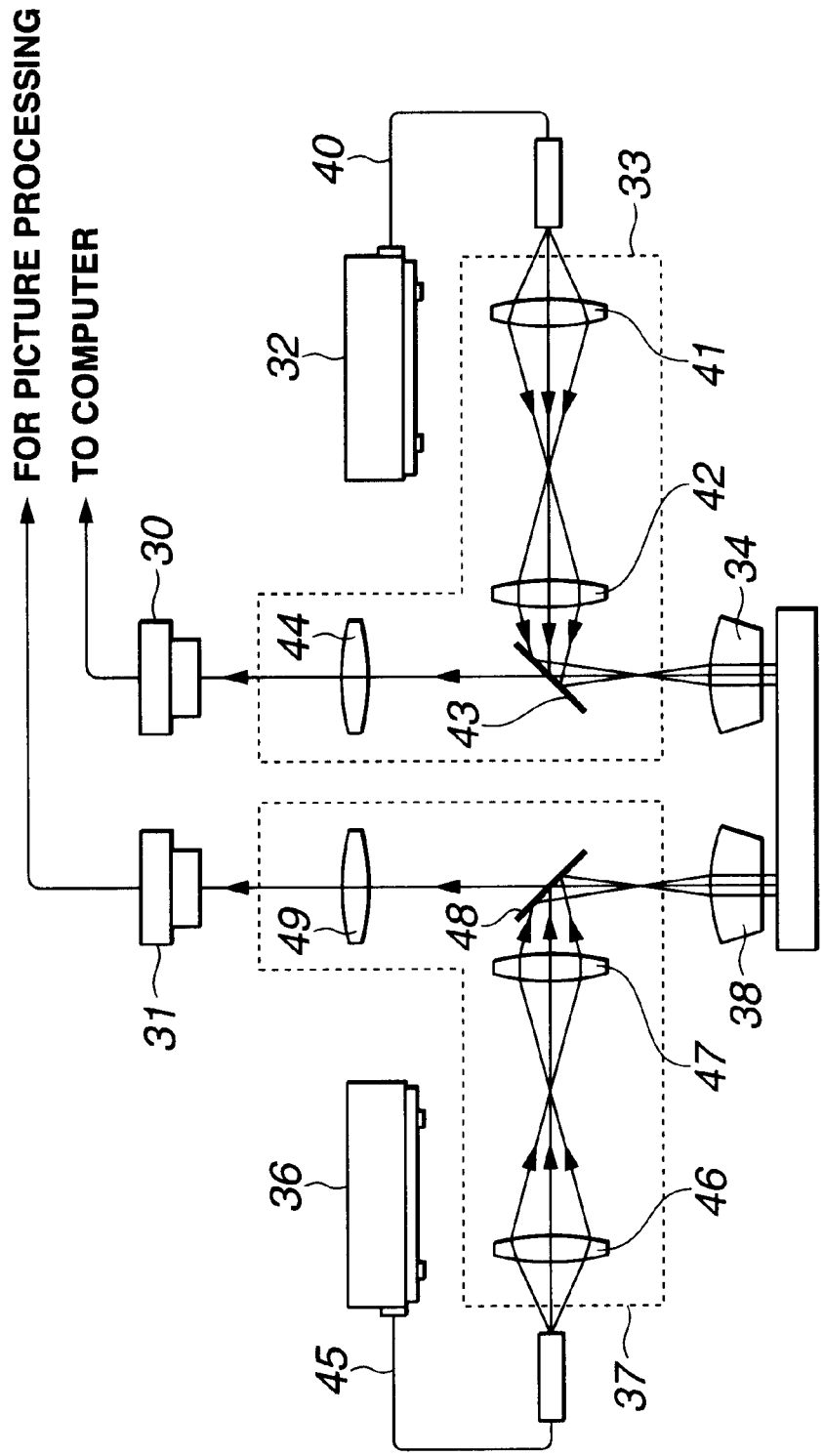
FIG. 5 shows an illustrative structure of an optical system of the optical unit of the inspection apparatus.

Referring to FIG. 5, the optical system of the optical unit 21 of the inspection apparatus 1 is explained in further detail by referring to FIG. 5a. Here, the explanation on the autofocussing units 35, 39 is omitted, whilst the optical system for illuminating the semiconductor wafer being inspected and the optical system for imaging the semiconductor wafer to be inspected are explained.

Referring to FIG. 5, the optical unit 21 includes a halogen lamp 32, an optical system for visible light 33 and an objective lens for visible light 34, as an optical system for photographing an image of a semiconductor wafer with the visible light.

The visible light from the halogen lamp 32 is transmitted over an optical fiber 40 to the optical system for visible light 33. The visible light, routed to the optical system for visible light 33, is first transmitted through two lenses 41, 42 to fall on a half mirror 43. The visible light, incident on the half mirror 43, is reflected by the half mirror 43 towards the objective lens for visible light 34 through which it falls on the semiconductor wafer. This illuminates the semiconductor wafer with visible light.

The image of the semiconductor wafer, illuminated by the visible light, is enlarged by the objective lens for visible light 34 and is transmitted through the half mirror 43 and an imaging lens 44 so as to be photographed by the CCD camera for visible light 30. That is, the reflected light from the semiconductor wafer, illuminated by the visible light, falls on the objective lens for visible light 34, half mirror 43 and the imaging lens 44 so that an enlarged image of the semiconductor wafer is photographed by the CCD camera for visible light 30. The image of the semiconductor wafer photographed by the CCD camera for visible light 30, referred to below as the visible image, is sent to the image processing computer 60.

The optical unit 21 includes, as an optical system for photographing an image of a semiconductor wafer a light source for UV laser light 36, an optical system for UV light 37 and an objective lens for UV light 38.

The UV light from the light source for UV laser light 36 is routed by an optical fiber 45 to the optical system for UV light 37. The UV light, routed to the optical system for UV light 37, is first transmitted through two lenses 46, 47 to fall on a half mirror 48. The visible light, incident on the half mirror 48, is reflected thereby towards the objective lens for UV light 38 through which it falls on the semiconductor wafer. This illuminates the semiconductor wafer with the UV light.

The image of the semiconductor wafer, illuminated by the UV light, is enlarged by the objective lens for UV light 38 and transmitted through the half mirror 48 and an imaging lens 49 so as to be photographed by the CCD camera for UV light 31. That is, the reflected light from the semi conductor wafer, illuminated by the UV light, falls on the CCD camera for UV light 31 through the objective lens for UV light 38, half mirror 48 and the imaging lens 49 so that an enlarged image of the semiconductor wafer is photographed by the CCD camera for UV light 31. The image of the semiconductor wafer, photographed by the CCD camera for UV light 31 (UV image) is routed to the image processing computer 60.

In the above-described inspection apparatus 1, in which an image of a semiconductor wafer can be photographed and inspected by the UV light shorter in wavelength than the visible lights finer defects can be detected and classified than in the case of using visible light for detection and classification.

Moreover, the inspection, apparatus 1 has both the optical system for visible light and that for the UV light, so that it is able to execute inspection of the semiconductor wafer at a low resolution using the visible light and that at a higher resolution using the UV light. Thus, it is possible with the inspection apparatus 1 to detect and classify larger defects by inspection of the semiconductor wafer at the low resolution using the visible light as well as to detect and classify smaller defects by inspection of the semiconductor wafer at the high resolution using the UV light.

In the inspection apparatus 1, the numerical aperture NA of the optical fiber 40 is preferably of a larger value, such as, for example, not less than 0.9. By employing a lens with a larger value of the numerical aperture NA as the optical fiber 40, it is possible to detect finer defects.

Meanwhile, if the defect of he semiconductor wafer is composed only of micro-irregularities, devoid of the color information, such as scratches, the defects can hardly be viewed with the incoherent light. If conversely the highly coherent light, such as. laser light, is used, even a defect composed only of micro-irregularities, devoid of the color information, such as scratches, can clearly be seen by light interference in the vicinity of the step difference of the micro-irregularities. That is, in the inspection apparatus 1, the phase information, difficult to detect with the visible light (incoherent light) from the halogen lamp 32, can easily be detected using the UV laser light (coherent light) from the light source for UV laser light 36.

Figure 6:
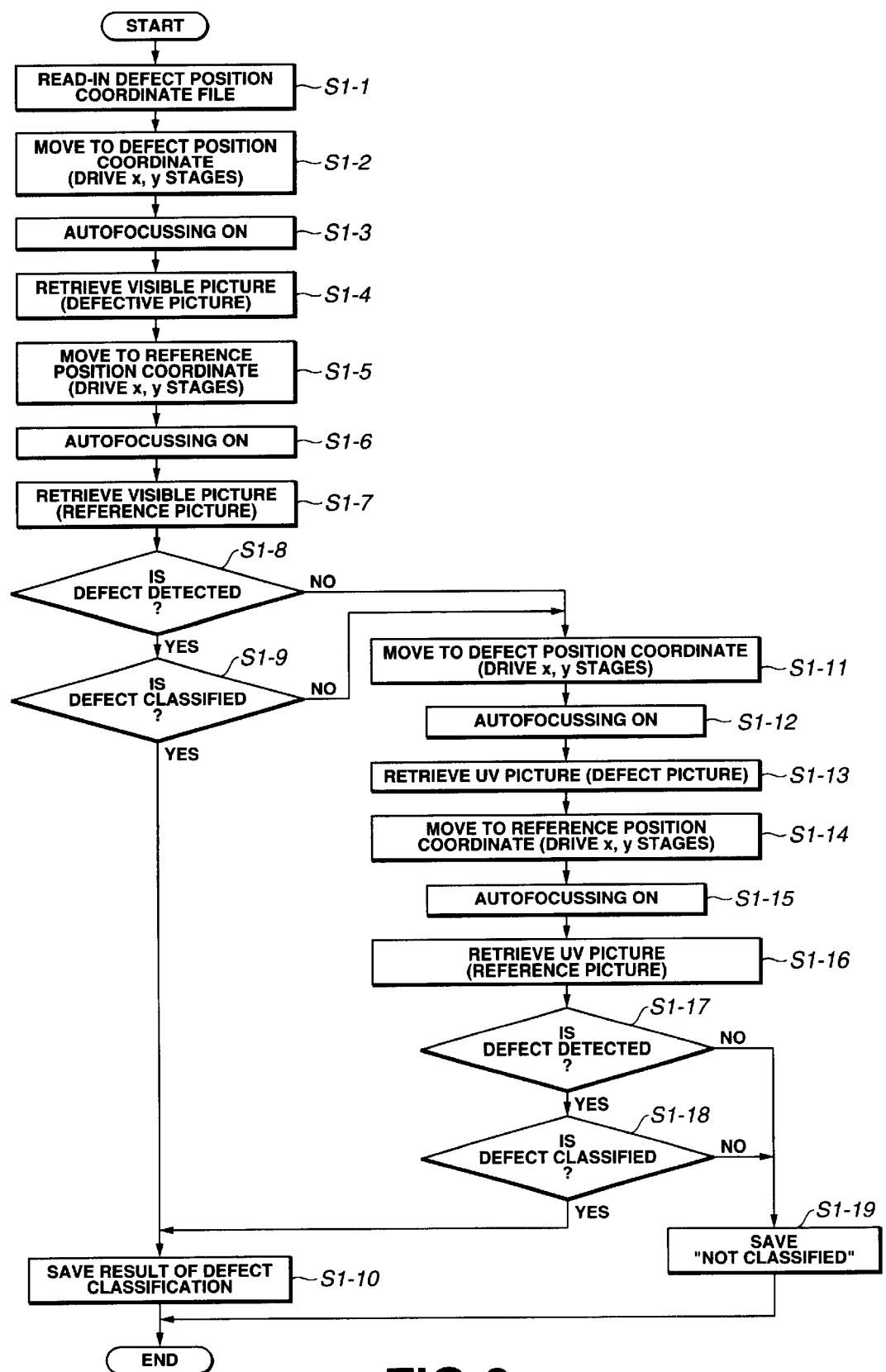
FIG. 6 is a flowchart showing a typical procedure in inspecting the semiconductor wafer in the inspection apparatus.

Referring to the flowchart of FIG. 6, a typical sequence of operations in inspecting a semiconductor wafer on the inspection apparatus 1 is explained. Meanwhile, the flowchart of FIG. 6 shows the sequence of processing operations as from the time when a semiconductor wafer to be inspected is placed on the inspection stage 14. The flowchart of FIG. 6 shows a typical sequence of operations when a defect on a semiconductor wafer is inspected and classified by the inspection apparatus 1 when the defect position on the semiconductor wafer is known from the outset. It is assumed that a large number of similar device patterns have been formed on the semiconductor wafer and that the detection and classification of defects are executed on photographing an image of a region suffering from defects (defect image) and an image of the other region and comparing the two images.

First, as shown at step S1-1, a defect position coordinate file is read into the control computer 61. It is noted that the defect position coordinate file is a file stating the information pertinent to defect positions on the semiconductor wafer and is prepared by previously measuring the defect position on the semiconductor wafer by, for example, a defect detection device. Here, the defect position coordinate file is read into the control computer 61.

Next, at step S1-2, the X-stage 15 and Y-stage 16 are moved by the control computer 61 to move the semiconductor wafer to a defect position coordinate indicated by the defect position coordinate file until the area of the semiconductor wafer to be inspected is in the visual field of the objective lens for visible light 34.

Next, at step S1-3, the autofocussing unit for visible light 35 is driven by the control computer 61 to execute autofocussing of the objective lens for visible light 34.

Next, at step S1-4, an image of the semiconductor wafer is photographed by the CCD camera for visible light 30 to route the photographed visible image to the image processing computer 60. Meanwhile, the visible image photographed here is an image in a defect position coordinate indicated by the defect position coordinate file, that is an image of a region retained to contain a defect.

Next, at step S1-5, the X-stage 15 and the Y-stage 16 are driven by the control computer 61 to move the semiconductor wafer to a reference position coordinate so that the reference region of the semiconductor wafer will be in the visual field of the objective lens for visible light 34.

It is noted that the reference region is a region of the semiconductor wafer other than the area thereof to be inspected, or a region in which there are formed device patterns similar to those in the area of the semiconductor wafer to be inspected.

Next, at step S1-6, the autofocussing unit for visible light 35 is driven by the control computer 61 to execute autofocussing of the objective lens for visible light 34.

At the next step S1-7, an image of the semiconductor wafer is photographed by the CCD camera for visible lights 30 to route the photographed visible image to the image processing computer 60. Meanwhile, the visible image photographed here is an image of an area of the semiconductor wafer where there are formed device patterns similar to those in the area of the semiconductor wafer to be inspected. This image is referred to below as a reference image.

Next, at step S1-8, the defect image retrieved at step S1-4 is compared by the image processing computer 60 to the reference image retrieved at step S1-7 to detect a defect from a defective imaged. If a defect has been detected, processing transfers to step S1-9 and, if otherwise, processing transfers to step S1-11.

At step S1-9, the image processing computer 60 scrutinizes into the sort of the defect to proceed to classification. If the defect could be classified, processing transfers to step S1-10 and, if otherwise, to step S1-11.

At step S1-10, the classified results of the defect are saved. These results of the defect are saved in a storage device connected to the image processing computer 60 or to the control computer 61. Meanwhile, the classified results of the defect may also be transferred to and saved in another computer connected over a network to the image processing computer 60 or to the control computer 61.

On completion of the processing at step S1-10, the classification of the defect of the semiconductor wafer is at an end. So, the processing comes to a close. If however there are plural defects on the semiconductor wafer, the processing may revert to step S1-2 to detect and classify other defects.

On the other hand, if no defect has been detected at step S1-8, or if no defect has been classified at step S1-9, processing transfers to step S11 ff., to effect imaging at high resolution using UV light to detect and classify the defect.

In such case, the X-stage 15 and Y-stage 16 are caused to be driven by the control computer 61 to shift the semiconductor wafer to a defect position coordinate indicated by the defect position coordinate file until the area of the semiconductor wafer to be inspected is within the visual field of the objective lens for UV light 38.

Next, at step S1-12, the autofocussing controller for UV light 39 is caused to be driven by the control computer 61 to effect autofocussing of the objective lens for UV light 38.

Next, at step S1-13, an image of the semiconductor wafer is photographed by the CCD camera for UV light 31. The photographed UV image is routed to the image processing computer 60. It is noted that the UV image photographed here is an image at the defect position coordinate indicated by the defect position coordinate file, that is the defective image. It is also noted that the defective image is to be photographed at a higher resolution than in photographing employing the visible light, using the UV light shorter in wavelength than the visible light.

Next, at step S1-14, the X-stage 15 and the Y-stage 16 are driven by the control computer 61 to shift the semiconductor wafer to a reference position coordinate until the reference region of the semiconductor wafer is in the visual field of the objective lens for UV light 38. It is noted that the reference region is a region other than the region of the semiconductor wafer to be inspected and is a region where there are formed device patterns similar to those in the region of the semiconductor wafer to be inspected.

Next, at step S1-15, the autofocussing controller for UV light 39 is caused to be driven by the control computer 61 to effect autofocussing of the objective lens for UV light 38.

Next, at step S1-16, an image of the semiconductor wafer is photographed by the CCD camera for UV light 31 to route the photographed UV image to the image processing computer 60. It is noted that the UV image photographed here is an image of the area where a device pattern similar to that in the area of the semiconductor wafer to be inspected, that is a reference image. It is also noted that the defective image is to be photographed at a higher resolution than in photographing employing the visible light, with use of the UV light shorter in wavelength than the visible light.

Then, at step S1-17, the defective image retrieved at step S1-13 and the reference image retrieved at step S1-16 are compared to each other by the image processing computer 60 to detect a defect from the defective image. If the defect has been detected, processing transfers to step S1-18 and, if otherwise, to step S1-19.

At step S1-18, the image processing computer 60 scrutinizes into the nature of the detected defect to effectuate classification. If the defect has been classified processing transfers to step S1-10 to save the classified results of the defect. If the defect has not been classified, processing transfers to step S1-19.

At step S1-19, the information indicating that the defect has not been classified is saved. The information indicating that the defect has not been classified is saved in e.g., a storage device connected to the image processing computer 60 or to the control computer 61. It is noted that this information may be transferred to and saved in an other computer connected lover the network to the image processing computer 60 or to the control computer 61.

By the above-described sequence of operations, the image photographed by the CCD camera for visible light 30 is processed and analyzed to inspect the semiconductor wafer at a low resolution. If the detection of classification of the defect with the visible light has not been made, the photographed image is processed and analyzed by the CCD camera for UV light 31 to effectuate semiconductor wafer inspection at a high resolution.

Figure 7:
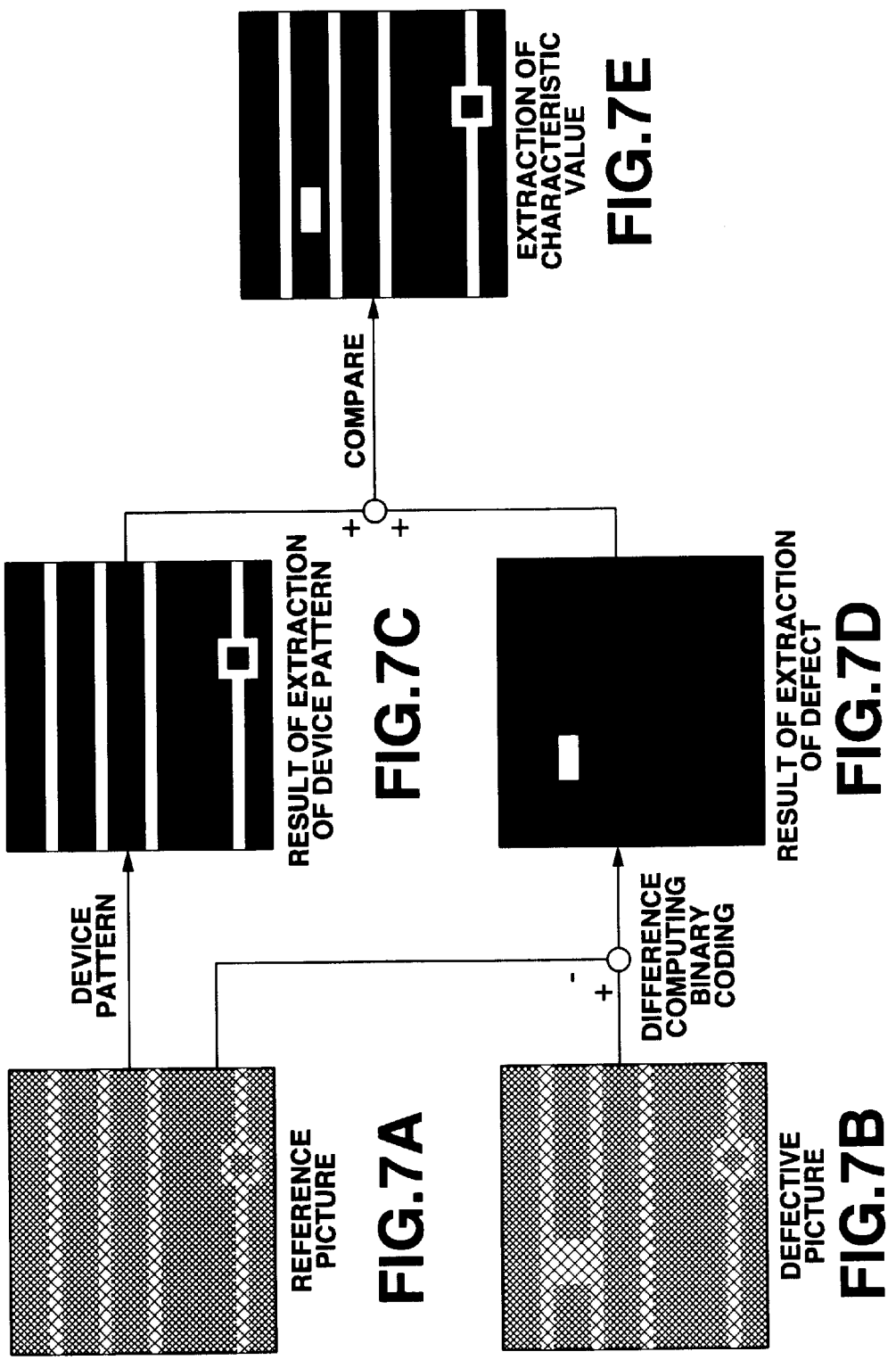
FIG. 7 illustrates the technique of detecting a defect from a reference image and a defective image.

Referring to FIG. 7, the technique of detecting a defect from the reference image and the defective image photographed by the CCD cameras 30, 31 is now explained.

FIG. 7a shows a typical image in the reference area, that is a reference image, in which there is formed a device pattern similar to a device pattern in an area being inspected, whilst FIG. 7b shows an image in a region under inspection, retained to be defective, that is a defective image.

In detecting a defect from the reference image and the defective image, a device pattern is extracted from the reference image, based on the color information or the gray scale information, as shown in FIG. 7c. Also, a differential image is found from the reference image and the defective image, and a portion representing a significant difference is extracted as a defect, as shown in FIG. 7d.

Next, an image corresponding to overlapped image of the image representing the extraction of the device pattern shown in FIG. 7c and the image representing the result of device extraction shown in FIG. 7d, is found, and the proportion of the defect in the device pattern, for example is extracted as a characteristic amount pertinent to the defect.

By the above technique, a defect can be detected by processing and analyzing the reference and defective images, photographed by the CCD cameras 30, 31, to inspect the semiconductor wafer.

In the inspection apparatus 1, in which the image photographed by the CCD camera for visible light 30 is processed and analyzed to inspect the semiconductor wafer at a low resolution and, if defect detection or classification with the visible light has not been feasible, the image photographed by the CCD camera for UV light 31 is processed and analyzed to inspect the semiconductor wafer at a high resolution, it is possible to detect and classify finer defects than is possible in case of defect detection and classification solely by the visible light.

However, a broader area can be imaged at a time if imaging is performed at a lower resolution using the visible light. So, if the defect is of a sufficiently large size, it is more efficient to inspect the semiconductor wafer at a lower resolution using the visible light from the outset. Therefore, the inspection of the semiconductor wafer can be realized more efficiently not by using the UV light from the outset to detect or classify the defect, but by using the visible light at the outset to detect or classify the defect.

Meanwhile, in the present inspection apparatus 1, the main body portion 10, in which the semiconductor wafer is to be inspected, is mounted within the clean box 3, and clean air is furnished to the inside of the clean box 3 to maintain high degree of cleanness to locally elevate only the degree of cleanness in the environment of inspection to enable the inspection to be carried out in a clean atmosphere.

However, in the inspection apparatus 1, configured as described above, contaminants such as powder debris tend to be produced in the clean box 3 as the inspection stage 14 or the transporting robot 23 is operated in inspecting the semiconductor wafer. If the contaminants produced in the clean box 3 become attached to the semiconductor wafer mounted on the inspection stage 14 or to the semiconductor wafer transported into the clean box 3 through the vessel 7, it becomes impossible to execute the inspection satisfactorily. So, in the inspection apparatus 1, it is critical to discharge contaminants produced in the clean box 3 to outside the clean box 3 promptly without allowing the contaminants to become attached to the semiconductor wafer.

In particular, in the present inspection apparatus 1, in which the light source for UV laser light 36 or the CCD camera for UV light 31 is used to inspect an extremely fine device pattern with the line width not larger than 0.18 $\mu$m to a high resolution, it is probable that fine contaminants, which raised no serious problem so far, prove factors prohibiting proper inspection.

Thus, in the present inspection apparatus 1, an air current in the clean box 3 is properly controlled to discharge contaminants, inclusive extremely fine ones, produced in the clean box 3, to outside the clean box 3 to prevent deposition thereof on the semiconductor wafer.

Specifically, in the present inspection apparatus 1, the volume of clean air supplied from the clean air unit 4 into the inside of the clean box 3 is individually controlled for each of the blowers 5a, 5b to freely control the air current in the clean box 3.

As a method for individually controlling the volume of clean air supplied from the clean air unit 4 into the inside of the clean box 3 for each of the blowers 5a, 5b, the numbers of revolutions of the blowers 5a, 5b may be adjusted individually. In the inspection apparatus 1, the blowers 5a, 5b are connected to the control computer 61 through the wind volume control interface 61f. The numbers of revolutions of the blowers 5a, 5b may be controlled by sending control signals to the blowers 5a, 5b from, the control computer 61 through the wind volume control interface 61f.

Thus, in the present inspection apparatus 1, it is possible to adjust the numbers of revolutions of the blowers 5a, 5b individually to control the wind volume of clean air supplied from the clean air unit 4 into the clean box 3 for each of the blowers 5a, 5b by an inspector inputting necessary commands through the input device 53b to the control computer 61.

The air supplied from the blowers 5a, 5b is freed of contaminants by being passed through a high-performance air filter to yield clean air which is sent as a downward flow into respective regions in the clean box 3 lying below the blowers 5a, 5b. It is noted that, if the wind volumes of the air from the blowers 5a, 5b remain the same, the wind velocity in the respective regions in the clean box 3 lying below these blowers 5a, 5b differs with the difference in the size of the respective regions which depend on e.g., the shape of the clean box 3 or on the arrangement of the main body portion 10 in the clean box 3. There are occasions wherein an unexpected perturbed air stream is produced due to difference in the wind velocity in the respective regions to blow up contaminants produced in the clean box 3 to permit these contaminants to become attached to the semiconductor wafer.

In the inspection apparatus 1, the numbers of revolution of the blowers 5a, 5b are individually adjusted to control the wind volume of the clean air furnished from the clean air unit 4 into the clean box 3 for each of the blowers 5a, 5b to provide for a uniform wind velocity in the respective regions in the clean box 3 to prevent contaminants effectively from becoming attached to the semiconductor wafer.

Moreover, for preventing the contaminants from becoming attached to the semiconductor wafer, it is highly effective to route the clean air supplied into the inside of the clean box 3 towards the inspection stage 14 on which the semiconductor wafer is set, or into the cassette 7b in which the semiconductor wafer is loaded. If the clean air is routed in this manner into the inside of the clean box 3 towards the inspection stage 14 on which the semiconductor wafer is set or into the cassette 7b in which the semiconductor wafer is loaded, it is possible not only to prevent turbulent air which has blown up contaminants effectively from intruding towards the inspection stage 14 or into the cassette 7b but also to remove contaminants incidentally attached to the semiconductor wafer mounted on the inspection stage 14 or loaded in the cassette 7b to discharge the so-removed contaminants effectively to outside the clean box 3.

In the inspection apparatus 1, in which the numbers of revolution of the blowers 5a, 5b are individually adjusted to control the wind volume of clean air supplied into the clean box 3 from the clean air unit 4 individually for each of the blowers 5a, 5b, to control the air stream in the clean box 3 properly, it is possible to route clean air onto the inspection stage 14 on which the semiconductor wafer is set, or into the cassette 7b in which the semiconductor wafer is housed, to prevent contaminants from becoming attached to the semiconductor wafer effectively.

Meanwhile, the air current in the clean box 3 can be visually checked using an air stream visualizing device. In this case, an inspector is able to check the air current in the clean box 3 visually to control the wind volume of the clean air supplied from the clean air unit 4 into the clean box 3 for each of the blowers 5a, 5b to provide for proper air flow in the clean box 3.

Figure 8:
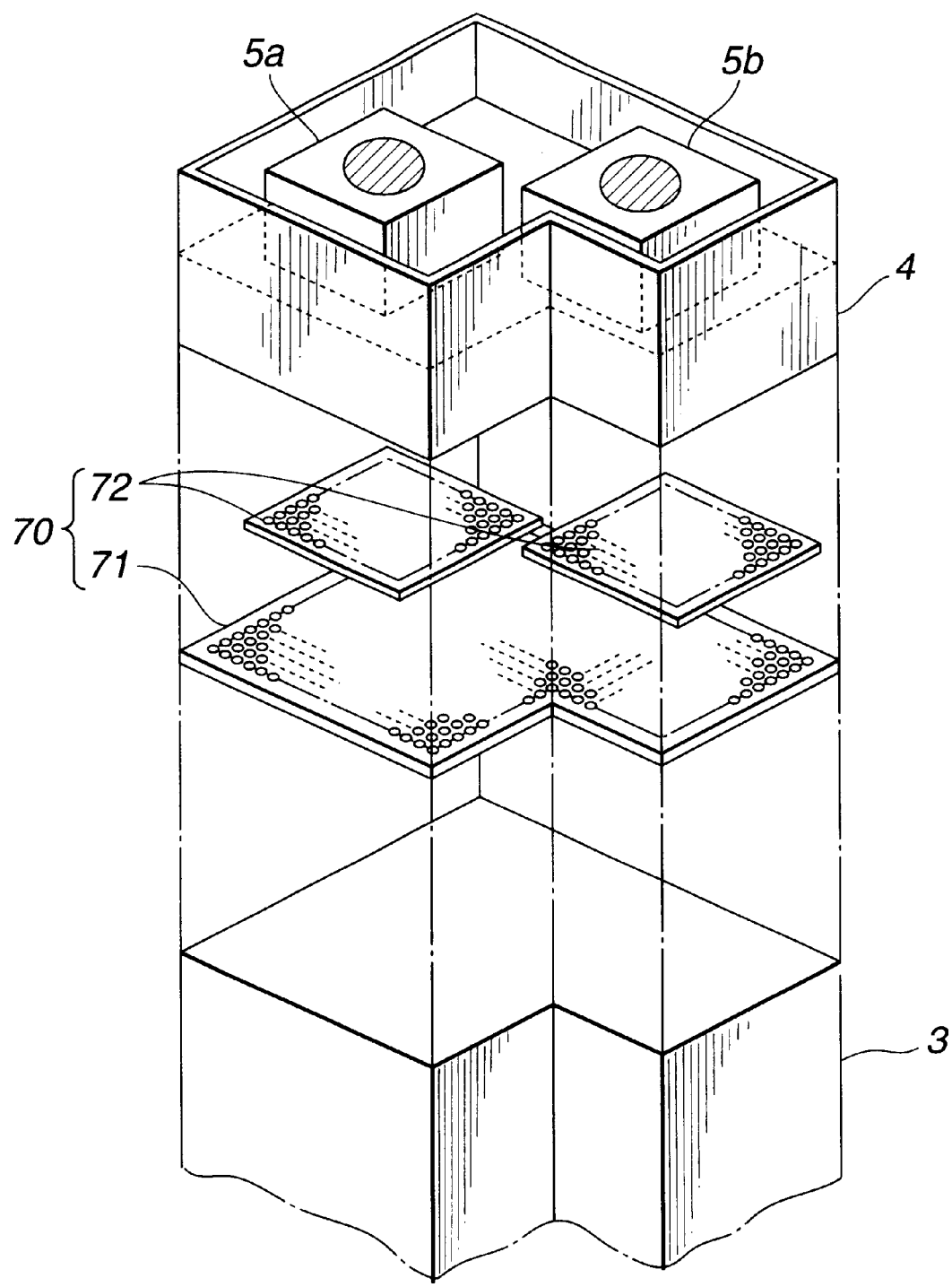
FIG. 8 is a schematically perspective view showing the state in which the clean box of the inspection apparatus is separated from the clean air unit.

As a method for individually controlling the wind volume of the clean air supplied from the clean air unit 41into the clean box 3, for each of the blowers 5a, 5b, it may be envisaged to provide a partitioning plate 70 having openings facing the clean box 3 of the clean air unit 4, and to adjust the opening ratio in areas of the partitioning plate 70 associated with the blowers 5a, 5b individually depending on which of the blowers 5a, 5b are associated with the areas of the partitioning plate 70, as shown in FIG. 8. Stated differently, by individually adjusting the opening ratio of the area of the partitioning plate 70 associated with the blower 5a and that of the area of the partitioning plate 70 associated with the blower 5b, it is possible to control the wind volume of the clean air supplied from the clean air unit 4 into the clean box 3 individually for each of the blowers 5a, 5b.

The partitioning plate 70, dividing the clean air unit 4 and the clean box 3 from each other, may, for example, be, constituted by perforated metal sheets 71, 72 each having a pre-set opening ratio. The opening ratio of the partitioning plate 70 may be varied by varying the manner of superposition of the two perforated metal sheets 71, 72 for the area of the partitioning plate 70 associated with the blower 5a and for the area of the partitioning plate 70 associated with the blower 5b to adjust the opening ratio of the partitioning plate 70 individually for the area of the partitioning plate 70 associated with the blower 5a and for the area of the partitioning plate 70 associated with the blower 5b.

Meanwhile, if a desirable value of the wind volume of clean air supplied from the area of the partitioning plate 70 associated with the blower 5a and a desirable value of the wind volume of clean air supplied from the area of the partitioning plate 70 associated with the blower 5b are known from the outset, perforated metal sheets each with an opening ratio corresponding to the desirable value of the wind volume may be provided in register with the blowers 5a, 5b for use as partitioning plate 70.

In the embodiment described above, the clean air unit 4 has the two blowers 5a, 5b. However, the number of the blowers may be determined in keeping with the size or the shape of the clean box 3, such that the clean box 3 may be provided with three or more blowers. In this case, the wind volume of the clean air supplied from the clean air unit 4 into the clean box 3 may be controlled individually from one blower to another.

Figure 9:
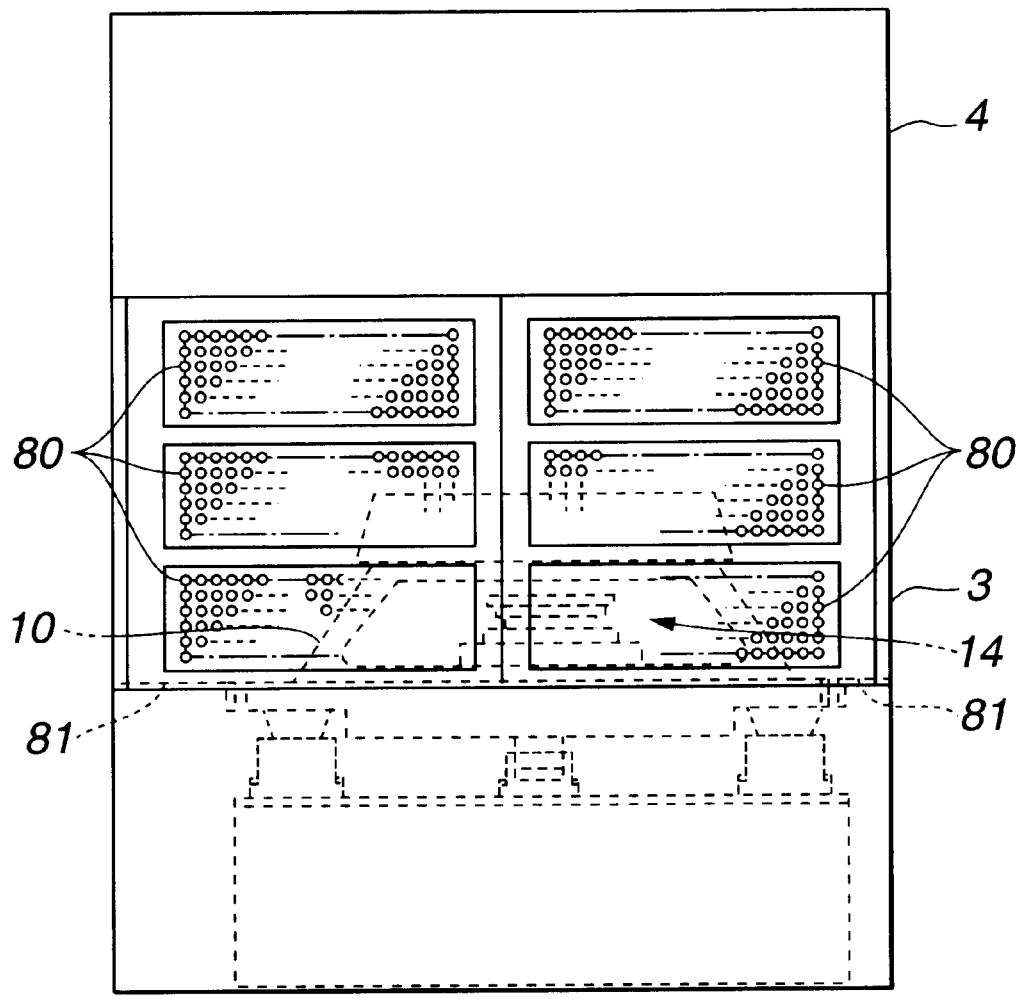
FIG. 9 is a side view showing the clean box of the inspection apparatus from a direction of an arrow A2 in FIG. 2

In the present inspection apparatus 1, opening areas 80 are provided in a lateral surface of the clean box 3 lying laterally of the inspection stage 14, in order to route the clean air supplied into the inside of the clean box 3 onto the inspection stage 14 carrying the semiconductor wafer thereon as shown in FIGS. 2 and 9. Meanwhile, FIG. 9 is a side view of the clean unit 2 looking in the direction of arrow A2 in FIG. 2.

Specifically, plural perforated metal sheets, each having a pre-set opening ratio, are fitted in a lateral surface of the clean box 3 lying laterally of the inspection stage 14, so that the portions of the lateral surface of the clean box 3 fitted with the perforated metal sheets operate as the opening areas 80. In the inspection apparatus 1, in which the opening areas 80 are provided in the lateral surface of the clean box 3 lying laterally of the inspection stage 14, part of clean air supplied as a downward flow from the clean air unit 4 into the inside of the clean box 3 may be passed over the inspection stage 14 towards the opening areas 80 provided laterally thereof, as described above, so as to be discharged through these opening areas 80 to outside the clean box 3.

Moreover, in the present inspection apparatus 1, a jutting portion 81 is provided on the lateral side of the clean box 3 for protruding inwards in order to route the clean air supplied into the inside of the clean box 3 onto the inspection stage 14 carrying thereon the semiconductor wafer, as shown in FIGS. 2 and 9. The jutting portion 81 divides the air chamber in the clean box 3 with the lower end of the inspection stage 14 as a boundary. This jutting portion 81, comprised of a perforated metal sheet of a pre-set opening ratio, routes a portion of clean air supplied from the clean air unit 4 as a downward flow towards the lower end of the clean box 3, while causing the other portion to flow laterally to above the inspection stage 14. Meanwhile, the jutting portion 81 is spaced a small distance from the main body portion 10, in order not to transmit vibrations generated in the clean box 3 to the main body portion 10. These vibration suppressing measures are highly effective in the present inspection apparatus 1 since the slightest vibrations prove hindrance to inspection.

By routing the clean air supplied from the clean air unit 4 onto the inspection stage 14 on which the semiconductor wafer is set and by allowing the clean air so routed to pass over the inspection stage 14, it is possible to prevent a turbulent air flow which has blown up the contaminants in the clean box 3 effectively from intruding to a region above the inspection stage 14.

Moreover, by routing clean air supplied from the clean air unit 4 to above the inspection stage 14, carrying thereon the semiconductor wafer, and by allowing the clean air so routed to flow over the inspection stage 14, it is possible to remove contaminants incidentally deposited on the semiconductor wafer set on the inspection stage 14 from the semiconductor wafer by the clean air to discharge them to outside the clean box 3 through the opening areas 80.

Meanwhile, in the present inspection apparatus 1, the opening areas 80 and the jutting portion 81, provided laterally of the inspection stage 14, may be formed by two perforated metal sheets overlapping with each other, with one of the perforated metal sheets being movable relative to the other, as in the case of the partitioning plate 70 described above. This feature is meritorious in that the opening ratios of the opening areas 80 and the jutting portion 81 can be varied freely to permit the air stream in the clean box 3 to be controlled advantageously.

In addition, in the present inspection apparatus 1, an opening area 90 is provided in a lateral surface of the clean box 3 in register with the cassette accommodating portion, to guide the clean air supplied into the clean box 3 into the inside of the cassette 7b, in which is loaded the semiconductor wafer, as shown in FIG. 1.

Specifically, there is fitted a perforated metal sheet of a pre-set opening ratio in a lateral surface of the clean box 3 in register with the cassette accommodating portion so as to serve as the opening area 90. In the inspection apparatus 1, in which the opening area 90 is provided in the lateral surface of the clean box 3 in register with the cassette 7b. As described above, part of the clean air supplied as a downward flow from the clean air unit 4 into the inside of the clean box 3 may be passed through the cassette 7b transferred into the clean box 3 to the opening area 90 and thence discharged to outside the clean box 3.

Figure 10:
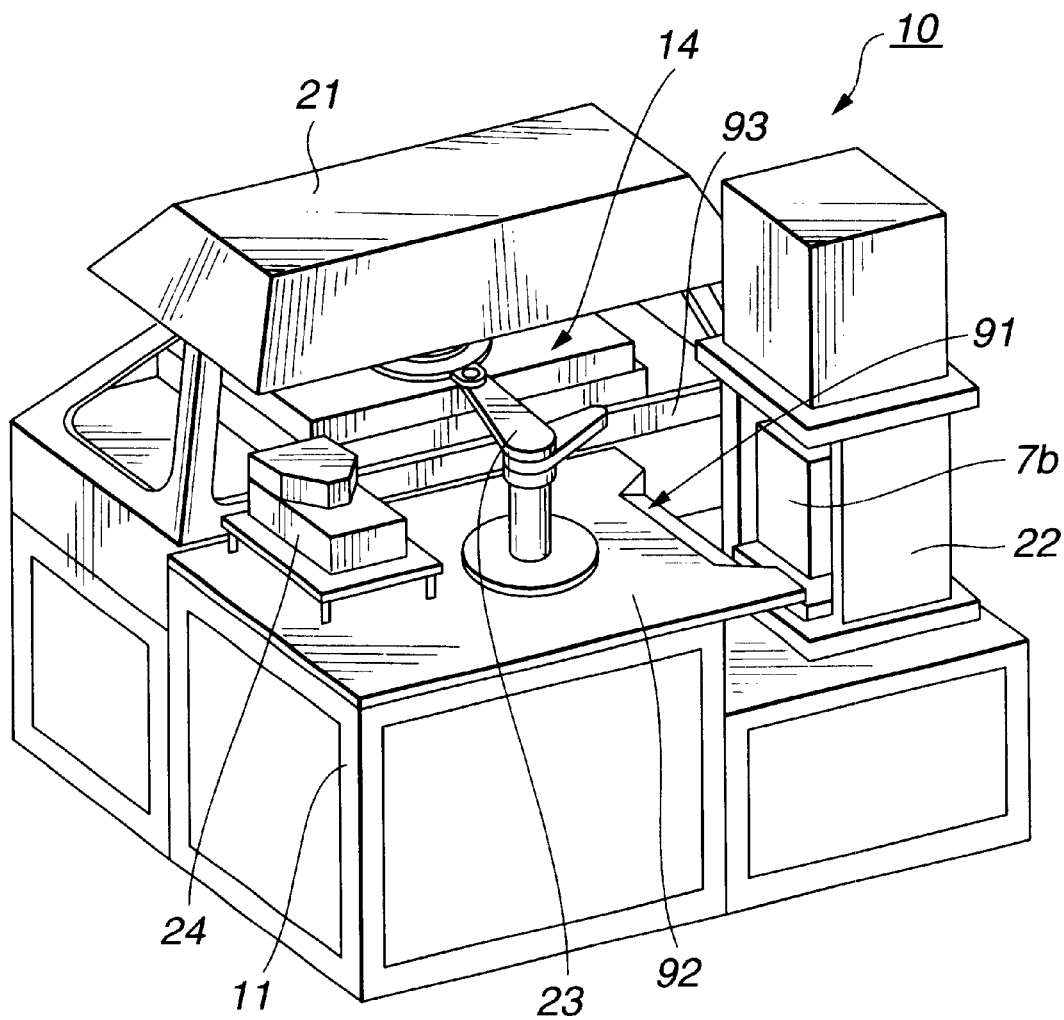
FIG. 10 is a perspective view showing the main body portion of the inspection apparatus.

Moreover, in the present inspection apparatus 1, an inclined guide 91, inclined towards the cassette accommodating portion, is provided in the vicinity of the cassette accommodating portion, in order to route the clean air supplied into the clean box 3 into the cassette 7b having the semiconductor wafer loaded therein, as shown in FIG. 10.

Specifically, there is provided, at the same height level as the jutting portion 81 provided on the clean box 3, a mounting plate 92 for mounting the transporting robot 23 and the pre-aligner 24. On one side of the mounting plate 92, there is provided an inclined guide 91 which is inclined towards the cassette accommodating portion. It is noted that FIG. 10 is a perspective view of the main body portion 10 in the clean box 3 looking from the sides of the elevator 22, transporting robot 23 and the pre-aligner 24.

By providing the inclined guide portion 91, inclined towards the cassette accommodating portion in the clean box 3, in the vicinity of the cassette accommodating portion, it is possible to route the clean air supplied into the clean box 3 by the inclined guide portion 91 into the cassette 7b having the semiconductor wafer loaded therein.

By routing clean air supplied from the clean air unit 4 into the cassette 7b having the semiconductor wafer loaded therein for passage through the cassette 7b, it is possible to remove contaminants incidentally affixed to the semiconductor wafer loaded in the cassette 7b from the semiconductor wafer by the clean air to permit the contaminants to be properly discharged to outside the clean box 3 through the opening area 90.

By routing clean air supplied from the clean air unit 4 into the cassette 7b, housing the semiconductor wafer therein, to pass the air therethrough, it is possible to remove contaminants incidentally attached o the semiconductor wafer loaded in the cassette 7b by the clean air to discharge the contaminants to outside the clean box 3.

Meanwhile, the opening area 90, provided lacteally of the cassette loading section in the clean box 3, may be constituted by two perforated metal sheets superposed together, with one of the sheets being movable with respect to the other, as in the case of the partitioning plate 70. In this case, since the opening ratio of the opening area 90 can be varied freely, the air stream in the clean box 3 can be controlled advantageously.

In the present inspection apparatus 1, there is provided a partitioning wall section 93 between an area of the main body portion 10 where there is provided the inspection stage 14 and an area thereof where there are provided the elevator 22, transporting robot 23 and the pre-aligner 24, as shown in FIG. 10.

The role of the partitioning wall section 93 is to prevent contaminants, such as fine dust, generated in the inspection stage 14 and its vicinity, from intruding into an area of the elevator 22, transporting robot 23 and the pre-aligner 24. Specifically, an upstanding piece of a pre-set height, formed integrally with the lower end of a support carrying the optical unit 21, performs the role of the partitioning wall section 93.

In the inspection apparatus 1, in which the partitioning wall section 93 is provided between the area of the main body portion 10 provided with the inspection stage 14 and that provided with the elevator 22, transporting robot 23 and the pre-aligner 24, for partitioning the two areas from each other, it is possible to prevent contaminants such as fine dust produced in the area of the inspection stage 14 from intruding into the cassette 7 along with the clean air supplied from the clean air unit 4 when introducing the clean air into the cassette 7b having the semiconductor wafer loaded therein.

In the foregoing description, the inspection apparatus 1 according to the present invention is assumed to be used in scrutinizing the nature of the defects in a semiconductor wafer. The inspection apparatus 1 according to the present invention may, however, be used for the objective other than that of discriminating the semiconductor wafer defects. That is, the inspection apparatus 1 according to the present invention may be used in order to check whether or not the device pattern formed on the semiconductor wafer has been formed to a desired pattern. The inspection apparatus 1 according to the present invention is also not limited to inspection of the semiconductor wafer and may be broadly applied to inspection of fine patterns. For example, the inspection apparatus 1 is effective in inspecting a flat panel display carrying a fine pattern.

What is claimed is:

1. An inspection apparatus comprising:

(a) a main body portion for inspecting an article for inspection;

(b) a clean box for accommodating the main body portion therein, wherein the clean box is provided with a jutting portion having a pre-set opening ratio at approximately the same height level as the lower end of the inspection stage, the jutting portion protruding towards the main body portion, and the distal end of the jutting portion is spaced a small distance from the main body portion;

(c) an air supplying unit including a plurality of blowers to control air volume individually to furnish clean air into the inside of the clean box;

(d) the main body portion being provided with an inspection stage on which the article for inspection is set and a cassette accommodating portion for carrying therein a cassette in which the article for inspection is loaded; and wherein there is provided a partitioning wall section between the inspection stage and the cassette accommodating portion for partitioning the inspection stage and the area of the cassette accommodating portion from each other;

(e) there being provided opening areas having a pre-set opening ratio in at least portions of a lateral surface of the clean box located laterally of the inspection stage and the cassette accommodating portion for allowing clean air supplied from the air supplying unit into the inside of the clean box to be passed over the inspection stage and through the cassette loaded in the cassette accommodating portion so as to be discharged to outside the clean box;

(f) a vibration dampening stage disposed within the main body, the vibration dampening stage further comprising an X-stage, Y-stage, Z-stage, and theta-stage, wherein the Y-stage is mounted on the X-stage, the theta-stage is mounted on the Y-stage, and the Z-stage is mounted on the theta-stage, the X and Y-stages being adapted to move horizontally, the X-stage moving horizontally perpendicular to the horizontal direction of the Y-stage, the theta-stage being adapted to move in a rotational direction, the Z-stage being adapted to move vertically, the vibration dampening stage being adapted to move in response to vibration.

* * * * *